United States Patent [19]

Walker

[11] 4,284,827
[45] Aug. 18, 1981

[54] PROCESS TO PREPARE METALATED OLEFINS

[75] Inventor: Jerry A. Walker, Kalamazoo, Mich.

[73] Assignee: The Upjohn Company, Kalamazoo, Mich.

[21] Appl. No.: 104,611

[22] Filed: Dec. 17, 1979

Related U.S. Application Data

[63] Continuation of Ser. No. 19,509, Mar. 12, 1979, abandoned.

[51] Int. Cl.$^3$ .................. C07C 41/18; C07C 41/24
[52] U.S. Cl. .................. 568/686; 568/56; 568/655; 564/341; 564/348; 564/463; 564/509
[58] Field of Search .................. 568/686, 681, 655, 56; 210/583 EE, 584 C, 570.5 R, 570.5 S, 609 AE, 571; 564/463, 341, 348, 509

[56] References Cited

PUBLICATIONS

Taskiner et al., Tetrahedron 32, pp. 563–565, (1976).
Arens Rec. Trav. Chem. 74, pp. 271–276, (1955).
Hunig et al., Ber. 91, pp. 380–392, (1958).
Farma et al., Ca. 56 7115, (1962).

Primary Examiner—Howard T. Mars
Attorney, Agent, or Firm—Bruce Stein

[57] ABSTRACT

Substituted ethanes (I) are reacted with an alkyl metal reagent to form isomeric metalated olefins (IIIA and IIIB) having a trans (IIIB) to cis (IIIA) ratio of greater than 70:30.

26 Claims, No Drawings

PROCESS TO PREPARE METALATED OLEFINS

This is a continuation of application Ser. No. 019,509, filed Mar. 12, 1979, now abandoned.

BACKGROUND OF THE INVENTION

Trans metalated olefins (IIIB) add to 17-keto steroids (1) better than the corresponding cis isomers (IIIA) to produce 16-unsubstituted pregnanes (5) which can be readily converted by methods well known to those skilled in the art to useful 16-substituted corticoids. The metalated olefins (IIIA and IIIB) are prepared from the corresponding olefin (IIA and IIB). It therefore is important to be able to prepare the olefin (II) with a very high trans to cis ratio. The known methods for producing the olefins (II) produce mixtures with a very low trans to cis ratio, just the opposite of what is desired for the synthesis of the 16-unsubstituted pregnanes. The present invention solves this problem by producing the olefin (II) with a trans to cis ratio of greater than 70:30.

J. F. Arens et al. in Rec. trav. chim. 77, 753 (1958) disclose a process to convert chloroacetaldehyde diethylacetal to 1-chloro-2-ethoxyethene by heating with acid catalysts. On page 755 the authors indicate that "The product consisted for the greater part of the cis-isomer." The present invention surprisingly and unexpectedly produces a trans cis ratio of greater than 70:30.

J. F. Arens also reported in Rec. trav. chim. 74, 271 (1955) dehydrohalogenating 1,2-dichloro-2-ethoxyethane to give 1-chloro-2-ethoxyethene. On page 274 Arens indicates that the product contained ". . . about 75% of the cis isomer and 25% of the lower boiling trans isomer."

S. Hunig and M. Kiessel in Chem. Ber. 91, 380 (1958) reported transforming 1,2-dichloro-2-ethoxyethane to 1-chloro-2-ethoxyethene by use of a tertiary amine and heat. Under the various reaction conditions reported the reaction produced predominantly the cis isomer.

German Offen. 2,210,010 reports the reaction of 1,1-dichloro-2-methoxyethane with methoxide to give 1-chloro-2-methoxyethene. The cis isomer was produced (54%) to a greater extent than the trans isomer (46%).

D. A. VanDrop et al. reported in Rec. trav. chim. 70, 289 (1951) the conversion of dichloroacetaldehyde diethylacetal to 1-chloro-2-ethoxyethene by use of activated zinc dust. The authors report (page 293), "The yield of the cis-isomer is found to be 4–5 times as great as that of the trans-isomer, . . . ".

M. Farina et al. reported in Rend. 1st Lombardo Sci. Pt. 1 Classe Sci. Mat. e Nat. 94A, 600 (1960) that the transformation of 1,2-dichloro-2-i-butoxyethane to 1-chloro-2-i-butoxyethene with a tertiary amine and hydrochloric acid gave a product which contained 75–90% of the cis isomer.

All of the above articles indicate that the trans isomer is produced to a much less extent than the cis isomer. These were empirical findings and the possible mechanistic reasons were not reported. However, in 1976 E. Taskinen and E. Sainio in Tetrahedron 32, 593 (1976) reported that based on thermodynamic calculations the cis isomer should predominate due to its lower enthalpy.

Therefore, based on both theoretical considerations as well as previous experiments reported in the chemical literature one skilled in the art would expect to have a trans to cis ratio much less than 50:50. However, the present invention (process) surprisingly and unexpectedly produces 1-chloro-2-alkoxyethene (II) with a trans cis ratio of greater than 70:30.

The only other method known to produce a mixture of 1-chloro-2-alkoxyethene (II) which is enriched in the trans isomer to greater than a 70:30 ratio is an indirect one, namely, production of the cis trans mixture by old methods and then fractional distillation.

SUMMARY OF THE INVENTION

Disclosed is a process for the preparation of compounds of the formulas:

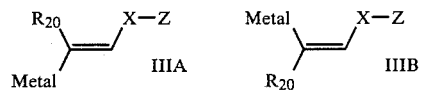

where the ratio of trans (IIIB) to cis (IIIA) isomers is greater than 70:30, which comprises reacting a compound of the formula:

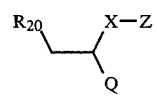

with a compound of the formula R-Metal in a temperature range of $-15°$ to $-120°$.

Also disclosed is a process for the preparation of compounds of the formulas:

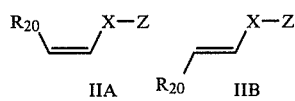

where the ratio of trans (IIB) to cis (IIA) isomers is greater than 70:30 which comprises reaction a compound of formula (I) with a compound of the formula R-Metal in a temperature range of $-15°$ to $-120°$. and quenching with a proton source.

The olefin (II) is useful as an intermediate in the production of a metalated olefin (III).

The metalated olefin (III) is useful in adding a two carbon side chain to a C-3 protected 17-keto steroid (2a-e) to produce a 16-unsaturated pregnane (5) which can be readily converted to useful 16-substituted corticoids.

DETAILED DESCRIPTION OF THE INVENTION

The desired metalated olefin (IIIB) is produced by reacting a substituted ethane (I) with a compound of the formula R-Metal in a temperature range of $-15°$ to $-120°$, see Chart A.

The substituted ethanes of formula (I) are either known to those skilled in the art or can readily be prepared from known compounds by methods well known to those skilled in the art. For the substituted ethane of formula (I), $R_{20}$ is a fluorine or chlorine atom or a —$NR_\alpha R_\beta$ group where $R_\alpha$ and $R_\beta$ are the same or different and are alkyl of 1 thru 3 carbon atoms. It is preferred that $R_{20}$ is a chlorine atom. X is an oxygen or sulfur atom, it is preferred that X is an oxygen atom. Z is alkyl of 1 thru 6 carbon atoms, phenyl or p-methylphenyl. It is preferred that Z is an alkyl group of 1 thru 4 carbon atoms, it is more preferred that Z is a methyl or ethyl group. Q is a good leaving group, a chlorine, bromine or iodine atom or a trimethylamino group. It is preferred that Q is a chlorine atom.

The compounds of the formula, R-Metal are either known to those skilled in the art or can readily be prepared from known compounds by methods well known to those skilled in the art. For the compound of the formula R-Metal, R is alkyl of 1 thru 5 carbon atoms and phenyl. It is preferred that R is a secondary group or a primary alkyl group of 1 thru 4 carbon atoms. The metal is lithium, sodium, or potassium. It is preferred that the metal is lithium. It is also preferred that the compound R-Metal is selected from the group consisting of n-butyl lithium, propyl lithium, s-butyl lithium, n-butyl potassium or i-propyl lithium. It is more preferred that R-Metal is n-butyl lithium.

The substituted ethane (I) and the R-Metal are mixed in a dry organic solvent. The organic solvent must be dry because if water is present it would react with the R-Metal necessitating the use of extra R-Metal. The preferred organic solvents are ethers such as THF, dimethoxyethane, diethyl ether, dioxane, etc. It is most preferred that the organic solvent is THF. The organic solvent may comprise a mixture of ether and hydrocarbon and/or aromatic solvents provided that the mixture contains at least some ether. It is preferred that the ether be present in as high a concentration as possible. The reaction is best performed in pure THF. The substituted ethane (I) can be added to the compound of the formula R-Metal or the other way around.

The reaction is performed in a temperature range of $-15°$ to $-120°$, preferably $-30°$ to $-90°$, more preferably at about $-60°$ to $-90°$. At higher temperatures the reaction proceeds faster than at the lower temperatures as is well known to those skilled in the art. The reaction is exothermic, therefore, the R-Metal reagent is added very slowly, usually over a period of 15 minutes to 1.5 hours. Because the reaction is exothermic the reaction mixture must be cooled to maintain a reaction temperature not greater than $-15°$. At $-90°$ the reaction is usually complete in about 1 hour while at $-30°$ the reaction is complete in about 15 minutes. At $-15°$ the reaction proceeds, however, the yield is low. Even though the yield is low, the ratio of trans (IIIB) to cis (IIIA) isomers is greater than 70:30.

If it is desired to isolate the olefin (II) the substituted ethane (I) is reacted with the R-Metal compound which produces a mixture of the olefin (II) and the metalated olefin (III). In order to assure that the starting material (I) is maximally utilized it is preferred that at least 1 equivalent of R-Metal be utilized, it is even more preferred that at least 2 equivalents of R-Metal be utilized. When the reaction is complete (about 1 hour) the reaction mixture is quenched with a proton source which converts any metalated olefin (III) to olefin (IIA and IIB). The proton source is any very mildly acidic compound such as water, an alcohol ($R_a$—OH), a carboxylic acid ($R_b$—COOH), sulfuric acid or ammonium salts. A sufficient amount is used but not so much that the pH of the reaction mixture becomes less than 6. It is preferred that the quenching agent is selected from the group consisting of water, methanol, ethanol, acetic acid or ammonium chloride. If it is desired to obtain pure trans olefin (IIB), it may be readily obtained by methods well known to those skilled in the art such as fractional distillation. The reaction mixture is then worked up as is well known to those skilled in the art.

If the metalated olefin (III) is the desired product of the process of the present invention then preferably greater than 1.5 equivalents of R-Metal/equivalent of substituted ethane (I) are used, more preferably 1.5–2 equivalents. The reaction is performed in the same manner and under the same conditions set forth above for the production of the olefin (II) except that 1.5–2 equivalents of R-Metal are preferred and the reaction is not quenched. The reaction mixture contains a ratio of trans (IIIB) to cis (IIIA) isomers of greater than 70:30. The metalated olefin mixture (IIIA and IIIB) enriched in the trans isomer (IIIB) or the pure trans metalated olefin (IIIB) is then reacted with a 17-keto steroid (1) in its protected form (2a–2e) to produce a 16-unsaturated pregnane (5) which is readily converted to a useful 16-substituted corticoid.

The 17-keto steroids (1) are well known to those skilled in the art or may readily be prepared from known compounds by methods well known to those skilled in the art. For example, the Δ1,4-17-keto steroids (1) are known, see U.S. Pat. No. 2,902,410, in particular Example 1. The Δ4,9(11)-17-keto steroids (1) are known, see U.S. Pat. No. 3,441,559, in particular Example 1. The 6α-fluoro-17-keto steroids (1) are known, see U.S. Pat. No. 2,838,492, in particular Examples 9 and 10. The 6α-methyl-17-keto steroids (1) are known, see U.S. Pat. No. 3,166,551 in particular Example 8.

The 16β-methyl-17-keto steroids (1) can readily be prepared from the corresponding 17-keto steroid (1) by the processes of U.S. Pat. Nos. 3,391,169 (Examples 75 and 76), 3,704,253 (Column 2 and Examples 1–3) and 3,275,666.

Chart B discloses the utility of the present invention. The 17-keto steroids (1) where $R_6$ is a hydrogen or fluorine atom or methyl group; wherein $R_{11}$ is a hydrogen atom, $\alpha$—$OR_{11a}$ or $\beta$—$OR_{11a}$; where $R_{11a}$ is a hydrogen atom or TMS with the proviso that when $R_{11}$ is —$OR_{11a}$, $=$ in ring C is a single bond; where $R_{16}$ is a hydrogen atom or methyl group; where ~ indicates the $R_{16}$ group can be in either the $\alpha$ or $\beta$ configuration and where $=$ is a single or double bond, must be protected at the C-3 position before reaction with the metalated olefin (III). The androst-4-ene-3,17-diones (1) are protected as the 3-enol ether (2a), 3-enamine (2b) or ketal (2c).

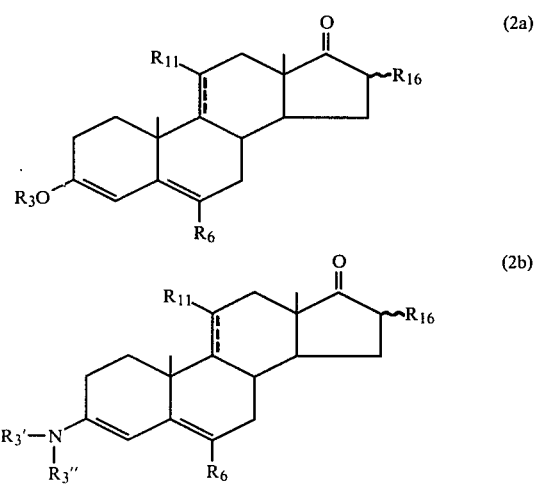

-continued

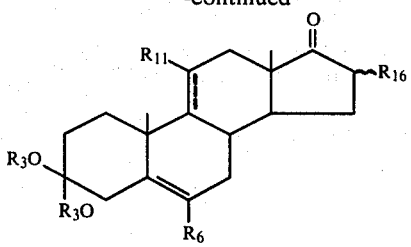
(2c)

where $R_3$ is alkyl of 1 thru 5 carbon atoms, with the proviso that with the ketal the $R_3$ groups can be connected to form the ethylene ketal; $R_3'$ and $R_3''$ are the same or different and are alkyl of 1 thru 5 carbon atoms. The enol ethers (2a) are prepared by methods well known in the art, see J. Org. Chem. 26, 3925 (1961), Steroid Reactions, Edited by Carl Djerassi, Holden-Day, San Francisco 1963, page 42–45, and U.S. Pat. No. 3,516,991 (Preparation 1). The 3-enamines (2b) are also prepared by methods well known in the art, see U.S. Pat. No. 3,629,298 and Steroid Reactions, supra, page 49–53. The ketals (3c) are also prepared by well known methods, see Steroid Reactions, supra, page 11–14. The androsta-1,4-diene-3,17-diones (1) are protected as the 3-dialkylenamine (2d) or ketal (2e)

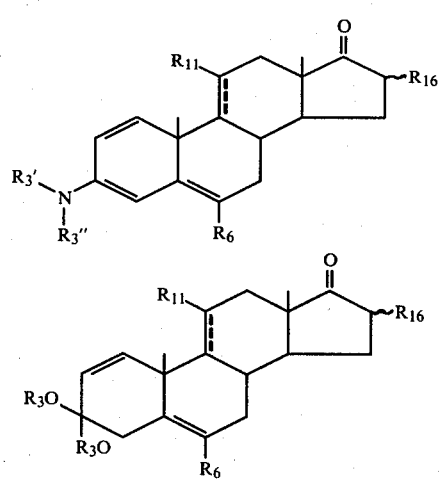

In Chart B, the compound of formula (2a) can be replaced by either the compound of formula (2b or 2c) all of which will produce the corresponding intermediate compound of the formula (3a, 3b or 3c), 21-aldehyde (4a) and 16-unsaturated pregnane (5a). Likewise with the Δ1 steroids the compound of formula (2d) can be replaced by the compound of formula (2e) which will produce the corresponding intermediate compound of the formula (3e), the 21-aldehyde (4b) and the 16-unsaturated pregnane (5b).

When $R_{11}$ is hydroxyl, either α or β, the hydroxyl group must be protected during the metalated olefin (organo lithium) reaction. The protecting group (TMS) can then be removed by means well known to those skilled in the art.

The protected 17-keto steroids (2a, 2b or 2c) are reacted with a metalated olefin (IIIA and IIIB) or (IIIB). The metalated olefins (IIIA and IIIB) are prepared according to the process of the present invention.

The cis-trans mixture (IIIA and IIIB) or trans (IIIB) metalated olefin in an inert aprotic solvent such as THF, pentane, diethyl ether, hexane, toluene is cooled to −100° to −20°, preferably between −60° and −30°, more preferably about −45° under an inert atmosphere such as nitrogen.

The protected 17-keto steroid (2a–2e) is suspended in an inert aprotic solvent such as those listed above or added as the solid. It is preferable to use the same solvent. The protected 17-keto steroid (2a–2e) is cooled to about −60° to −30°, preferably to about −45°. The metalated olefin (IIIA and IIIB) or (IIIB) and the protected 17-keto steroid (2a–2e) are then contacted at a temperature below −25°, preferably about −60° to −35°. The metalated olefin (IIIA and IIIB) or (IIIB) can be added to the protected steroid (2a–2e) or the protected steroid can be added to the metalated olefin (III). In order to avoid side reactions it is important to premix the substituted ethane (I) with the metal-base prior to the contacting with the protected 17-keto steroid (2a–2e).

The olefin intermediate (3a–3e) can be isolated after about 0.5–20 hours, preferably about 3 hours, if it is so desired by quenching the reaction with a suitable quenching agent such as water, $R_{17a}$-W, $(R_{17a}CO)_2O$ or $R_{17a}COM$ where $R_{17a}$ is alkyl of 1 thru 3 carbon atoms, thereby $R_{17}$ is a hydrogen atom, alkyl of 1 thru 3 carbon atoms or an acyl group of 2 thru 4 carbon atoms. M is a chlorine or bromine atom. W is a bromine or iodine atom. Preferred quenching agents include methyl iodide, methyl bromide, and ethyl iodide. Most preferred is methyl iodide.

Alternatively and preferably the olefin intermediate (3a–3e) is not isolated but is hydrolyzed by acid, greater than 1 equivalent being required, preferably about 6 equivalents. The particular acid is not critical, acids such as sulfuric, phosphoric, hydrochloric, acetic, citric, benzoic are all suitable. The reaction mixture is warmed to about 25°–50° and stirred until the reaction is complete as measured by TLC. The reaction mixture is worked up by the usual methods and concentrated to give the crude 21-aldehyde (4). When one starts with the protected Δ4-3-keto steroid (2a–2c) the 21-aldehyde (4) produced will obviously be the 21-aldehyde (4a). Likewise when one practices the process of the present invention beginning with the protected Δ1,4-3-keto steroid (2d or 2e) the 21-aldehyde (4) produced will be the 21-aldehyde (4b). The term 21-aldehyde (4) when used is meant to apply to and include both 21-aldehydes (4a and 4b) when appropriate. The 21-aldehyde (4) is crystallized from solvents such as methylene chloride-heptane. When the 17-keto steroid (1) is androst-4,9(11)-diene-3,17-dione and the metalated olefin is trans-2-chloro-1-ethoxy-2-lithioethene or a trans-cis (IIIA and IIIB) mixture with a ratio of greater than 70:30 the yield of the 21-aldehyde (4) for 4 experiments was 86.6, 86.7, 84.0 and 83.5% chemical yield, see Examples 4–7.

The 21-aldehyde (4) is a mixture of the 2 geometrical isomers

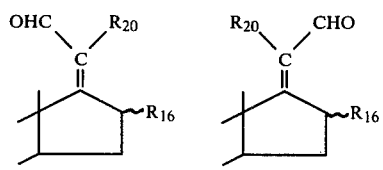

formed in approximately equal amounts. The isomeric 21-aldehydes (4) can be separated if desired but for the purposes of the present invention it is not necessary and even undesirable to do so since both isomeric 21-aldehydes (4) are converted to the desired 16-unsaturated pregnane (5).

Chart C discloses an alternative, but less preferred, process for producing the 21-aldehyde (4) which is via an isolatable intermediate (3f or 3g). The isolatable intermediates (3f and 3g) are obtained from (3a–3c) and (3d and 3e) respectively by reaction with a compound such as phosphorous oxychloride (POCl$_3$) with a co-reagent base such as pyridine at about $-45°$. The respective products (3f and 3g) are then transformed to the desired 21-aldehyde (4) by reaction with an acid as described above for the compounds (3a–3c) and (3d and 3e).

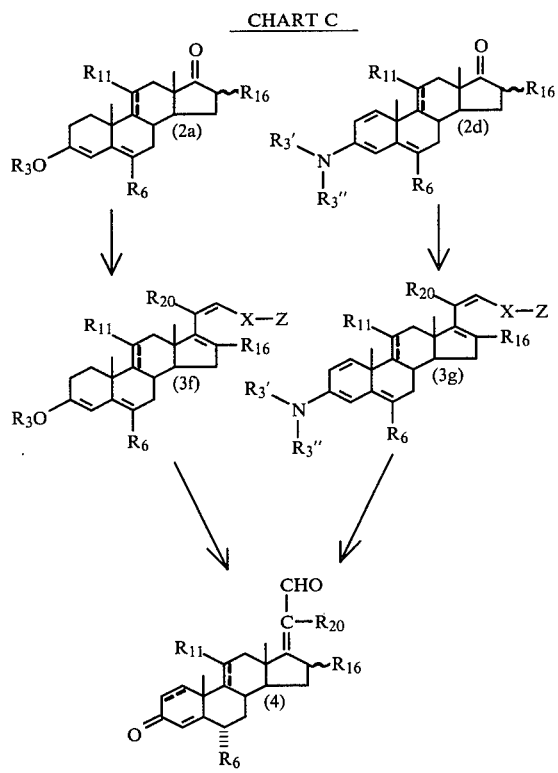

CHART C

The formulas for the compounds (3a–3g) all show the double bond at C$_{20}$ to be trans. When the metalated olefin (III) is a cis-trans mixture then the double bond at C$_{20}$ of the compounds (3a–3g) would be a mixture of cis and trans isomers. When the metalated olefin (III) is the trans isomer than the double bond at C$_{20}$ will of course be trans. In the specification and examples when the cis-trans nature of the C$_{20}$ bond is not specified it will have the geometry as that of the starting metalated olefin compound (III) as is well known to those skilled in the art. Whether the C$_{20-21}$ double bond is cis-trans or just trans in the compounds of formula (3) is not of great importance inasmuch as upon acid hydrolysis they are both converted to the identical 21-aldehyde (4) which in itself exists in two geometrically isomeric forms. It is understood that the formula for the 21-aldehyde (4) is meant to and does represent both isomeric 21-aldehydes. Again, it is not critical as to which 21-aldehyde isomer is obtained inasmuch as both are converted to the identical 16-unsaturated pregnane (5).

During the acid hydrolysis of the compound of formulas (3a–3d) to the 21-aldehyde (4) the protecting group is removed from these five compounds regardless of whether they were protected as an ether, enamine or ketal and the desired 21-aldehyde (4) is obtained as the 3-keto compound.

In the case of enamines (3b, 3d and 3g) if the reaction medium is a little too acidic it should be neutralized with a base to a pH of approximately 3 to 4 which is preferable for removal of the enamine protecting group.

The 21-aldehydes (4) are converted to the corresponding 16-unsaturated pregnane (5) by reaction with an alkali metal or alkaline earth metal salt of a carboxylic acid of the formula R$_{21}$COOH in a polar organic solvent. When the 21-aldehyde (4) is saturated at C$_1$ (4a) the 16-unsaturated pregnane (5) obtained is the corresponding C$_1$ saturated 16-unsaturated pregnane (5a). When the 21-aldehyde (4) is the Δ1,4-compound (4b) the corresponding Δ1,4-16-unsaturated pregnane (5b) is obtained. The term 16-unsaturated pregnane (5) is meant to include and apply to both 16-unsaturated pregnanes (5a and 5b) when appropriate. R$_{21}$ is alkyl of 1 thru 5 carbon atoms or phenyl. Suitable salts of these acids include, for example, potassium acetate, sodium acetate, magnesium propionate, calcium butyrate and sodium benzoate. Suitable organic solvents for the reaction include DMF, pyridine, THF, DMAC and the like. It is preferred the organic solvent be DMF and the salt be sodium or potassium acetate. The reaction is conducted in the range of 50°–200°, preferably 100°–150° depending on the particular 21-aldehyde (4), the salt and the solvent and is usually complete in 4–8 hours. The process is best performed by using crystalline 21-aldehyde (4) and adding it slowly to a mixture of DMF and acetate at about 120° under nitrogen. The reaction is monitored by TLC, ethyl acetate-hexane (1:1). When the reaction is complete it is cooled and an organic solvent such as toluene is added. The mixture is extracted twice with sodium chloride (5%) and back washed twice with an organic solvent. The organic solvents are combined, dried and concentrated under reduced pressure to give the 16-unsaturated pregnanes (5), see Example 8.

The 16-unsaturated pregnanes (5) are useful in the synthesis of a number of anti-inflammatory cortical steroids. If the substituents R$_6$ and R$_{16}$ are hydrogen and in the final product it is desired they not be hydrogen they can be transformed to the desired substituent within the scope of their definition by means well known to those skilled in the art. If unsaturation is not present at C-1 and it is desired, the compound may be dehydrogenated by known means. If substitution at R$_6$, R$_{16}$ or unsaturation at C-1 or C-9(11) is desired these substituents may be added to the 17-keto steroid (1) before beginning the synthesis thereby having the desired substitution in the molecule when the 16-unsaturated pregane (5) is obtained.

In particular, 21-acetoxypregna-4,9(11),16-triene-3,20-dione (5) is a very useful intermediate in the synthesis of commercially valuable steroids. It is well known to those skilled in the art that the 16-unsaturated pregnanes (5) can be transformed to 16α-hydroxy, 16α-methyl and 16β-methyl steroids.

For example both U.S. Pat. No. 2,864,834 and J. Am. Chem. Soc. 78, 5693 (1956) describe procedures for transforming 21-acetoxypregna-4,9(11),16-triene-3,20-dione (5) to 9α-fluoro-11β,16α,17α,21-tetrahydroxy-pregna-1,4-diene-3,20-dione (triamcinolone). J. S. Mills et al. in J. Am. Chem. Soc. 82, 3399 (1960) describe a method by which 21-acetoxypregna-4,9(11),16-triene- 3,20-dione (5) could readily be transformed to 6α,9α-difluoro-11β,16α,17α,21-tetrahydroxypregna-1,4-diene-3,20-dione 16,17-acetonide (fluocinolone acetonide).

U.S. Pat. No. 3,923,985 describes a process for the introduction of a 16α-methyl group into 21-acetoxy-pregna-1,4,9(11),16-tetraene-3,20-dione (5) to give 21-acetoxy-16α-methylpregna-1,4,9(11)-triene-3,20-dione which by methods well known to those skilled in the art can be converted to 16α-methyl steroids such as 6α-fluoro-11β,17α,21-trihydroxy-16α-methylpregna-1,4-diene-3,20-dione (paramethasone) and its 21-acetate; 9α-fluoro-11β,17α,21-trihydroxy-16α-methylpregna-1,4-diene-3,20-dione (dexamethasone) and 6α,9α-difluoro-11β,17α,21-trihydroxy-16α-methylpregna-1,4-diene-3,20-dione (flumethasone).

DEFINITIONS

The definitions and explanations below are for the terms as used throughout the entire patent application including both the specification and claims.

All temperatures are in degrees Centigrade.

TLC refers to thin-layer chromatography.

GC refers to gas chromatography.

THF refers to tetrahydrofuran.

TMS refers to trimethylsilyl.

DMSO refers to dimethylsulfoxide.

DMF refers to dimethylformamide.

SSB refers to an isomeric mixture of hexanes.

DMAC refers to dimethylacetamide.

PMR refers to proton magnetic resonance spectroscopy, chemical shifts are reported in ppm (δ) downfield from TMS.

When solvent pairs are used, the ratio of solvents used are volume/volume (v/v).

R is alkyl of 1 thru 5 carbon atoms or phenyl.

$R_3$ is alkyl of 1 thru 5 carbon atoms with the proviso that with the ketal the $R_3$ groups can be connected to form the ethylene ketal.

$R_6$ is a hydrogen or fluorine atom or methyl group.

$R_{11}$ is a hydrogen atom, α —$OR_{11\alpha}$ or β —$OR_{11\alpha}$ with the proviso that when $R_{11}$ is —$OR_{11\alpha}$, ≡ in ring C is a single bond.

$R_{11\alpha}$ is a hydrogen atom or TMS.

$R_{16}$ is a hydrogen atom or methyl group.

$R_{17}$ is a hydrogen atom, alkyl of 1 thru 3 carbon atoms or an acyl group of 2 thru 4 carbon atoms.

$R_{17\alpha}$ is alkyl of 1 thru 3 carbon atoms.

$R_{20}$ is a fluorine or chlorine atom or —$NR_\alpha R_\beta$.

$R_{21}$ is a alkyl of 1 thru 5 carbon atoms or phenyl.

$R_3'$ and $R_3''$ are the same or different and are alkyl of 1 thru 5 carbon atoms.

$R_\alpha$ and $R_\beta$ are the same or different and are alkyl of 1 thru 3 carbon atoms.

$R_a$ is alkyl of 1 thru 4 carbon atoms.

$R_b$ is alkyl of 1 thru 6 carbon atoms or phenyl.

M is a chlorine or bromine atom.

Q is a chlorine, bromine, iodine atom or trimethylamino group.

W is a bromine or iodine atom.

X is an oxygen or sulfur atom.

Z is alkyl of 1 thru 6 carbon atoms, phenyl or p-methylphenyl.

Metal is lithium, sodium, or potassium.

~ indicates the $R_{16}$ group can be in either the α or β configuration.

≡ is a single or double bond.

When the term "alkyl of — thru — carbon atoms" is used, it includes isomers of the alkyl group when such exist.

EXAMPLES

Without further elaboration, it is believed that one skilled in the art can, using the preceding description, practice the present invention to its fullest extent. The following preferred specific embodiments are, therefore, to be construed as merely illustrative, and not limiting of the preceding disclosure in any way whatsoever.

EXAMPLE 1    1-Chloro-2-ethoxyethene (IIa and IIb)

1,2-Dichloro-1-ethoxyethane (Ia, 153 mg., 90% purity) and THF (1 ml.) are cooled to below −40° under nitrogen. n-Butyl lithium in hexane (1.5 M, 1.35 ml.) is added dropwise over about 5 minutes. The mixture is stirred for 20 minutes at less than −40°. Water (100 μl) is added and the mixture brought to 20°–25°. The solution is analyzed by PMR which indicates a ratio of trans:cis 1-chloro-2-ethoxyethene of 78:22.

Example 2    1-Chloro-1-deutero-2-ethoxyethane

Following the procedure of Example 1, but quenching the reaction with D₂O (100 μl) instead of water, the title compound is obtained. Upon PMR analysis the ratio of trans:cis 1-chloro-1-deutero-2-ethoxyethene is about 80:20.

Example 3    Preparation of 20-chloropregna-4,9(11),17(20)-trien-3-on-21-al (4a) utilizing 1-chloro-2-ethoxyethene (IIa and IIb) as 1-chloro-2-ethoxy-1-lithioethene (IIIa and IIIb)

1,2-Dichloro-1-ethoxyethane (Ia, 1.84 g., 90% purity) and dry THF (12 ml.) are placed under nitrogen and cooled to below −45°. n-Butyl lithium in hexane (1.45 M, 15.5 ml.) is added dropwise over about 18 minutes. The mixture is stirred an additional 30 minutes and 3-hydroxyandrosta-3,5,9(11)-trien-17-one 3-methyl ether (2a, U.S. Pat. No. 3,516,991, 2.16 g.) is added all at once. The mixture is stirred for 3.25 hours at about −40° and then allowed to warm to −10°. Aqueous hydrochloric acid (6 N, 1.8 ml.) is added and the organic solvents are removed under reduced pressure. The residue is dissolved in methylene chloride (7.2 ml.) and aqueous hydrochloric acid (6 N, 9 ml.) and stirred for 18 hours at 20°–25°. The reaction mixture is then diluted with methylene chloride (20 ml.) and water (60 ml.). The organic layer is separated and washed with water (2×50 ml.), dried over sodium sulfate and concentrated under reduced pressure to a residue. This material is dissolved in methylene chloride (3.15 ml.) with stirring and heptane (26 ml.) is added dropwise over 45 minutes. The resulting slurry is stirred at 0°–5° for 30 minutes and then filtered. The solids are washed with heptane-methylene chloride (95:5, 2.25 ml.) and pentane (2×3 ml.) and then dried at about 50° under reduced pressure to give 20-chloropregna-4,9(11),17(20)-trien-3-on-21-al (4a).

EXAMPLE 4
20-Chloropregna-4,9(11),17(20)-triene-3-on-21-al (4a)

Anhydrous THF (250 ml.) and 1,2-dichloro-1-ethoxyethane (I, 22 ml., 25.1 g.) are cooled to −65° under nitrogen. n-Butyl lithium (323 mmole) is added dropwise over 60 minutes keeping the temperature below −65°. This is followed by a 10 ml. hexane rinse. The mixture is stirred for about 60 minutes. 3-Hydroxyandrosta-3,5,9(11)-triene-17-one 3-methyl ether (2a, 33.1 g.) is added all at once. The mixture is stirred 3 hours, and then warmed to −45° for 1 hour. The cooling is stopped and the mixture is warmed to 0°. Water (14 ml.) is added followed by hydrochloric acid (6 N, 140 ml.). The mixture is stirred for about 12 hours at 20°–25°. Methylene chloride (600 ml.) and water (600 ml.) are added. The phases are separated and the aqueous phase is extracted with methylene chloride (2×25 ml.). The organic phases are washed with water (400 ml.) and potassium carbonate (10%, 150 ml.). The combined methylene chloride extracts are dried and concentrated to give the crude chloroaldehyde (IV).

The solid is redissolved in methylene chloride (56 ml.) and heptane (45 ml.) is added. The mixture is seeded and heptane (350 ml.) is added dropwise over about 2.2 hours. The slurry is stirred for 1 hour at 20°–25°, 1 hour at 0°, filtered and the solids washed with heptanemethylene chloride (95:5) and hexane (2×25 ml.) and dried to give an isomeric mixture of the title compound, 33.1 g. (86.6% chemical yield). PMR (CDCl$_3$) 1.02, 1.1, 1.37, 5.55, 5.75, 9.7 and 9.9δ.

Following the general procedure of Example 4 and making non-critical variations, Examples 5, 6, and 7 give the following yields (chemical)

| Example | Yield (Chemical) % |
|---------|-------------------|
| 5 | 86.7 |
| 6 | 84.0 |
| 7 | 83.5 |

Example 8
21-Hydroxypregna-4,9(11),16-triene-3,20-dione-21-acetate (5a)

Anhydrous sodium acetate (5.8 g.) and DMF are stirred and heated at 120° under nitrogen. Crystalline 20-chloropregna-4,9(11),17(20)-trien-3-on-21-al (4a, Example 4, 12 g.) is added by adding 2 gm. every 20 minutes. The mixture is stirred for 90 minutes at 120°, the reaction is cooled and toluene (100 ml.) is added. The mixture is extracted with sodium chloride (5%, 2×100 ml.) and backwashed with toluene (2×20 ml.). The toluene phase is dried over magnesium sulfate and concentrated under reduced pressure to give the title compound, m.p. 120°–124°, PMR (CDCl$_3$) 0.89, 1.35, 2.18, 4.95, 5.55, 5.72 and 6.74δ.

CHART A

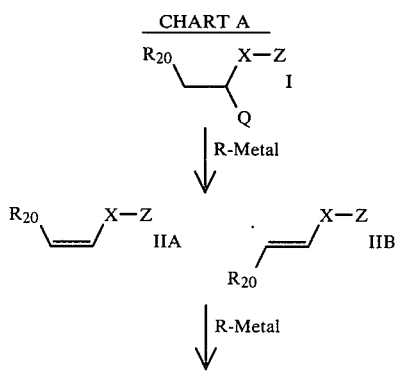

-continued
CHART A

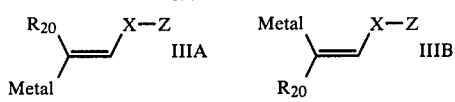

CHART B

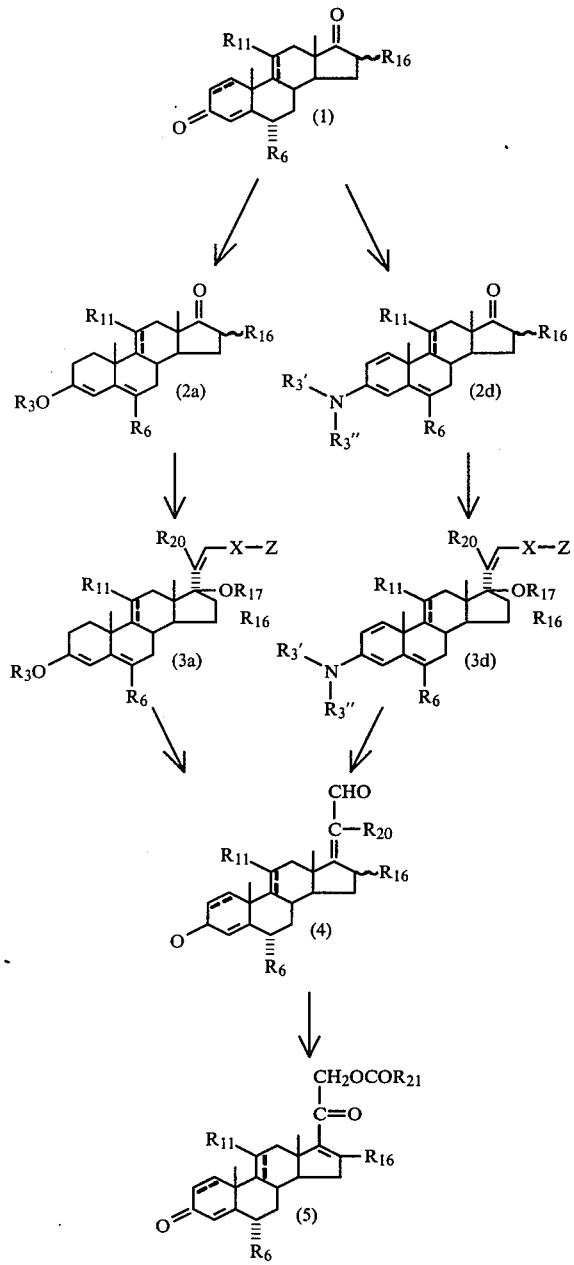

I claim:
1. A process for the preparation of compounds of the formulas:

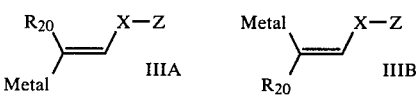

where $R_{20}$ is a fluorine or chlorine atom or a $-NR_\alpha R_\beta$ group where $R_\alpha$ and $R_\beta$ are the same or different and are alkyl of 1 thru 3 carbon atoms; where X is an oxygen or sulfur atom; where Z is alkyl of 1 thru 6 carbon atoms, phenyl or p-methylphenyl where the ratio of trans (IIIB) to cis (IIIA) isomers is greater than 70:30, which comprises reacting a compound of the formula:

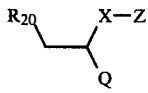 I where Q is a chlorine, bromine or iodine or iodine atom or a trimethylamino group with at least 1.5 equivalents of a compound of the formula R-Metal where R is alkyl of 1 thru 5 carbon atoms or phenyl; where metal is lithium, sodium, or potassium, in a dry organic solvent in a temperature range of $-15°$ to $-120°$.

2. A process according to claim 1 where 1.5–2 equivalents of R-Metal are used.

3. A process according to claim 1 where the metal is lithium.

4. A process according to claim 3 where R-Metal is n-butyl lithium.

5. A process according to claim 1 where the ratio of trans (IIIB) to cis (IIIA) isomers is greater than 75:25.

6. A process according to claim 1 where $R_{20}$ is a chlorine atom.

7. A process according to claim 1 where X is an oxygen atom.

8. A process according to claim 1 where Z is a methyl or ethyl group.

9. A process according to claim 8 where Z is ethyl.

10. A process according to claim 1 where Q is a chlorine atom.

11. A process according to claim 1 where the reaction is performed in a temperature range of $-30°$ to $-90°$.

12. A process for the preparation of compounds of the formulas:

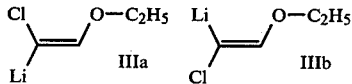

where the ratio of trans (IIIb) to cis (IIIa) isomers is greater than 70:30 which comprises reacting a compound of the formula:

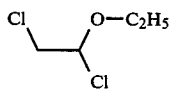 Ia with 1.5–2 equivalents of n-butyl lithium in a dry organic solvent in a temperature range of $-45°$ to $-90°$.

13. A process for the preparation of compounds of the formulas:

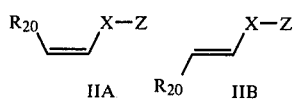

where the ratio of trans (IIB) to cis (IIA) isomers is greater than 70:30 which comprises (1) reacting a compound of the formula:

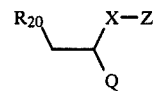 I with at least 1 equivalent of a compound of the formula R-Metal in a dry organic solvent in a temperature range of $-15°$ to $-120°$ and (2) quenching with a proton source so that the pH of the reaction mixture does not become less than 6, where $R_{20}$, X, Z, Q, Metal and R are defined in claim 1.

14. A process according to claim 13 where at least 2 equivalents of a compound of the formula R-Metal are used.

15. A process according to claim 13 where the proton source is selected from the group consisting of water, an alcohol of the formula $R_aOH$ where $R_a$ is alkyl of 1 thru 4 carbon atoms, a carboxylic acid of the formula $R_b$—COOH where $R_b$ is alkyl of 1 thru 6 carbon atoms or phenyl, ammonium salts or sulfuric acid.

16. A process according to claim 15 where the proton source is water, methanol, ethanol, acetic acid or ammonium chloride.

17. A process according to claim 13 where the metal is lithium.

18. A process according to claim 17 where R-Metal is n-butyl lithium.

19. A process according to claim 13 where the ratio of trans (IIB) to cis (IIA) isomers is greater than 75:25.

20. A process according to claim 13 where $R_{20}$ is a chlorine atom.

21. A process according to claim 13 where X is an oxygen atom.

22. A process according to claim 13 where Z is a methyl or ethyl group.

23. A process according to claim 13 where Z is ethyl.

24. A process according to claim 13 where Q is a chlorine atom.

25. A process according to claim 13 where the reaction is performed in a temperature range of $-30°$ to $-90°$.

26. A process to prepare compounds of the formulas:

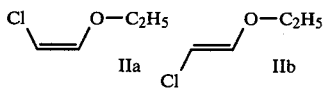

where the ratio of trans (IIb) to cis (IIa) isomers is greater than 70:30 which comprises reacting a compound of the formula

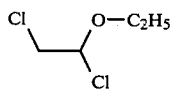

with greater than 2 equivalents of n-butyl lithium in a dry organic solvent in a temperature range of $-30°$ to $-90°$ and then quenching with water.

* * * * *